US010994079B2

(12) United States Patent
Kim

(10) Patent No.: US 10,994,079 B2
(45) Date of Patent: May 4, 2021

(54) SEMIAUTOMATIC SYRINGE WITH IMPROVED SAFETY

(71) Applicant: Hwi Hwa Kim, Jecheon-si (KR)

(72) Inventor: Hwi Hwa Kim, Jecheon-si (KR)

(73) Assignee: Hwi Hwa Kim, Jecheon-si (KR)

(*) Notice: Subject to any disclaimer, the term of this patent is extended or adjusted under 35 U.S.C. 154(b) by 437 days.

(21) Appl. No.: 16/076,397

(22) PCT Filed: Dec. 20, 2017

(86) PCT No.: PCT/KR2017/015105
§ 371 (c)(1),
(2) Date: Aug. 8, 2018

(87) PCT Pub. No.: WO2018/230792
PCT Pub. Date: Dec. 20, 2018

(65) Prior Publication Data
US 2020/0222631 A1     Jul. 16, 2020

(30) Foreign Application Priority Data

Jun. 15, 2017  (KR) .................. 10-2017-0076088

(51) Int. Cl.
*A61M 5/20*     (2006.01)
*A61M 5/152*    (2006.01)
(Continued)

(52) U.S. Cl.
CPC .......... *A61M 5/2053* (2013.01); *A61M 5/152* (2013.01); *A61M 5/16813* (2013.01);
(Continued)

(58) Field of Classification Search
CPC ............... A61M 5/2053; A61M 5/152; A61M 5/16813; A61M 5/3202; A61M 5/484;
(Continued)

(56) References Cited

U.S. PATENT DOCUMENTS 7,789,857 B2     9/2010 Moberg et al.
2008/0255543 A1* 10/2008 Tanaka .............. A61M 5/14276
604/891.1

FOREIGN PATENT DOCUMENTS

EP     0528977 A1    3/1993
JP     5528263 B2    6/2014
(Continued)

*Primary Examiner* — Amber R Stiles
(74) *Attorney, Agent, or Firm* — Harness, Dickey & Pierce, P.L.C.

(57) ABSTRACT

The present invention provides a semiautomatic syringe with improved safety including: a main body; a receptacle which is installed at one side of the main body, receives therein a set amount of infusion solution, and has a set pressure; an infusion solution tube which extends by a set length while penetrating the main body, connects with the receptacle, and provides a passageway for moving the infusion solution; a protective cover which is installed at the other side of the main body, connects with the infusion solution tube, extends by a set length, and has a hollow portion; an injection needle which is provided in the protective cover and has an injection hole formed to discharge the infusion solution, which moves through the infusion solution tube, to the outside; and a flow rate adjusting member which is installed in the main body and adjusts a movement amount of the infusion solution by opening and closing the passageway of the infusion solution tube, in which the injection needle is provided in a state of being inserted into the hollow portion of the protective cover, and a part of the injection needle protrudes to the outside of the protective cover by a change in pressure in the receptacle when the passageway of the infusion solution tube is opened, thereby achieving a more convenient, economic, and safe usage.

4 Claims, 7 Drawing Sheets

(51) Int. Cl.
    *A61M 5/168*     (2006.01)
    *A61M 5/32*     (2006.01)
    *A61M 5/48*     (2006.01)
    *A61M 39/28*     (2006.01)
    *A61M 5/31*     (2006.01)

(52) U.S. Cl.
    CPC ........ *A61M 5/3135* (2013.01); *A61M 5/3202* (2013.01); *A61M 5/484* (2013.01); *A61M 39/285* (2013.01); *A61M 2005/006* (2013.01)

(58) Field of Classification Search
    CPC .............. A61M 39/285; A61M 5/3135; A61M 2005/006
    See application file for complete search history.

(56) References Cited

FOREIGN PATENT DOCUMENTS

| | | |
|---|---|---|
| JP | 2014-168695 A | 9/2014 |
| KR | 10-2000-0069546 | 11/2000 |
| KR | 10-0365163 | 12/2002 |
| KR | 10-2012-0127720 | 7/2014 |
| KR | 10-2016-0086360 | 7/2016 |

\* cited by examiner

SEMIAUTOMATIC SYRINGE WITH IMPROVED SAFETY

CROSS-REFERENCE TO RELATED APPLICATIONS

This application is a National Phase of, and claims priority under 35 U.S.C. § 371 to, Korean PCT International Application No. PCT/KR2017/015105, which has an international filing date of Dec. 20, 2017, which claims benefit of, and further claims priority to Korean Application No. 10-2017-0076088, filed Jun. 15, 2017, the entire contents of each of which are hereby incorporated by reference.

TECHNICAL FIELD

The present invention relates to a semiautomatic syringe with improved safety which may achieve a more convenient and safe usage with a configuration in which an infusion solution may be automatically injected by contraction of rubber and a configuration in which an injection needle is inserted into a cover and the injection needle protrudes in a pop-up manner by a pressure only when the injection needle is used.

BACKGROUND ART

In general, a patient who gets an injection of growth hormone, a patient with diabetes, or a patient with erectile dysfunction sometimes gives himself/herself an injection of a therapeutic infusion solution at home in accordance with prescription of a medical practitioner, as necessary.

Here, various disposable syringes are used to inject the infusion solution into the body, and a disposable syringe typically used in the related art is configured to inject an infusion solution in a cylinder into the body through a needle while sticking the needle into a skin of the body and pressing a piston rod.

However, the disposable syringe in the related art, which is configured as described above, requires a user to directly and manually press the piston rod, and as a result, there is a problem in that it is difficult and inconvenient to use the syringe, and there are an inefficiency and an inconvenience in using the syringe because there is no means for easily adjusting a flow rate.

In addition, in a case in which the syringe is configured in a state in which the needle is exposed, there is concern that considerable dangerous and unhygienic situations will be caused and the needle will be contaminated, and even though a cover for protecting the needle is provided, there is a problem in that it is inconvenient to cover the needle with the cover or separate the cover.

Meanwhile, these syringes are sometimes used for domestic animals or pets, and particularly, when the syringes are used for animals such as cows having comparatively large bodies, the animals may be terrified while the user inserts the needles into the skins of the animals, which may cause a difficult situation to the user such as a situation in which the animals rave.

DOCUMENT OF RELATED ART

Patent Document

Korean Patent No. 10-0365163 (Title of the Invention: Device for Automatically Injecting Injection Solution)

DETAILED DESCRIPTION OF INVENTION

Technical Problem

The present invention has been made in an effort to solve the aforementioned problems in the related art, and an object of the present invention is to provide a semiautomatic syringe with improved safety which may achieve a more convenient and safe usage with a configuration in which an infusion solution may be automatically injected by contraction of rubber and a configuration in which an injection needle is inserted into a cover and the injection needle protrudes in a pop-up manner by a pressure only when the injection needle is used.

In addition, another object of the present invention is to provide a semiautomatic syringe with improved safety in which a configuration for opening and closing a movement passage of an infusion solution is additionally installed, and the opening-closing configuration is comparatively simply designed, such that it is possible to freely and easily adjust a flow rate of the infusion solution, simplify processes, and reduce production costs.

In addition, still another object of the present invention is to provide a semiautomatic syringe with improved safety in which a cover and a syringe body are configured to be separable from each other, and as a result, it is possible to freely replace not only the cover but also an injection needle, thereby enabling a hygienic usage.

Technical Solution

To achieve the aforementioned object, a semiautomatic syringe with improved safety according to the present invention may include: a main body; a receptacle which is installed at one side of the main body, receives therein a set amount of infusion solution, and has a set pressure; an infusion solution tube which extends by a set length while penetrating the main body, connects with the receptacle, and provides a passageway for moving the infusion solution; a protective cover which is installed at the other side of the main body, connects with the infusion solution tube, extends by a set length, and has a hollow portion; an injection needle which is provided in the protective cover and has an injection hole formed to discharge the infusion solution, which moves through the infusion solution tube, to the outside; and a flow rate adjusting member which is installed in the main body and adjusts a movement amount of the infusion solution by opening and closing the passageway of the infusion solution tube, in which the injection needle is provided in a state of being inserted into the hollow portion of the protective cover, and a part of the injection needle protrudes to the outside of the protective cover by a change in pressure in the receptacle when the passageway of the infusion solution tube is opened.

In addition, the receptacle may be a restoring member which has an internal pressure set in a state in which the restoring member expands by receiving the infusion solution, contracts by restoring force when the passageway of the infusion solution tube is opened, and discharges the received infusion solution to the infusion solution tube as the internal pressure is changed.

In addition, the flow rate adjusting member may include: a guide groove which is formed in the main body in a longitudinal direction; a support portion is formed in the guide groove in a longitudinal direction; a catching projection which has an inclined surface inclined inward from the support portion and protrudes to face the infusion solution tube; and a pressing roller which is coupled to the guide groove so that a central axis of the pressing roller traverses the inclined surface of the catching projection, and adjusts a degree of pressing the infusion solution tube by being closely attached to or spaced apart from the infusion solution tube while being moved along the guide groove and the inclined surface by external force.

In addition, the flow rate adjusting member may include: an enlarged portion which protrudes at a part of the infusion solution tube so that the passageway is enlarged; a watertight guide groove which is formed in a longitudinal direction at a side facing the enlarged portion and hydraulically sealed by elastic sealing processing; a pressing clamp which is installed in the enlarged portion and has an inclined surface at one side thereof; a guider which is connected to the pressing clamp and exposed to the outside of the infusion solution tube through the watertight guide groove so as to be held by a user, and correspondingly moves the pressing clamp while sliding along the watertight guide groove by external force; and a pressing ball which is installed in the enlarged portion and closes or opens the passageway of the infusion solution tube by being closely attached to or spaced apart from the inclined surface of the pressing clamp in accordance with a movement of the guider.

In addition, the protective cover may be separably coupled to the main body.

Effect of Invention

The semiautomatic syringe with improved safety according to the present invention may be used more conveniently, economically, and safely with the configuration in which the infusion solution may be automatically injected by the contraction of the receptacle made of rubber, and the configuration in which the injection needle is inserted into the protective cover, and the injection needle protrudes in a pop-up manner by a change in pressure in the receptacle only when the injection needle is used.

In addition, the flow rate adjusting member for opening and closing the movement passage of the infusion solution is additionally installed, and the configuration of the flow rate adjusting member is designed as the comparatively simple tube pressing structure or passageway closing structure, and as a result, it is possible to freely and easily adjust a flow rate of the infusion solution, simplify processes, and reduce production costs.

In addition, since the protective cover is configured to be separable from the main body, it is possible to freely replace not only the protective cover but also the injection needle, thereby enabling a hygienic usage.

BEST MODE

Figure 1:
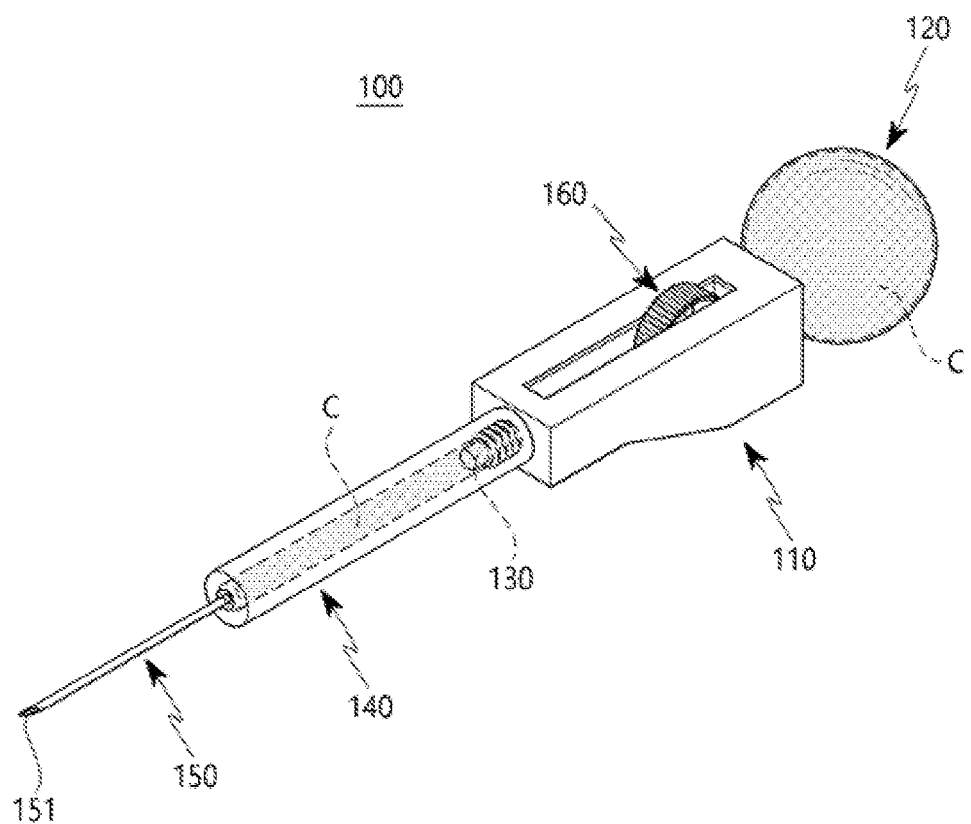
FIG. 1 is a perspective view of a semiautomatic syringe with improved safety according to an exemplary embodiment of the present invention.

The present invention will be described below with reference to the accompanying drawings that illustrate particular exemplary embodiments embodied by the present invention. The exemplary embodiments will be described in detail sufficiently so that those skilled in the art can carry out the present invention. It should be understood that the various exemplary embodiments of the present invention are different from one another but need not be exclusive to one another. For example, particular shapes, structures and features described herein related to one exemplary embodiment can be implemented as other exemplary embodiments without departing from the technical spirit and the scope of the present invention. In addition, it should be understood that positions or arrangements of respective constituent elements in the disclosed exemplary embodiments can be modified without departing from the technical spirit and the scope of the present invention. Therefore, the following detailed descriptions are not restrictive, and the scope of the present invention will be defined only by the appended claims and the entire scope equivalent to the claims. Similar reference numerals in the drawings indicate the same or similar functions in various aspects.

Hereinafter, exemplary embodiments of the present invention will be described in detail with reference to the accompanying drawings so that those skilled in the technical field to which the present invention pertains may easily carry out the exemplary embodiments.

Figure 2:
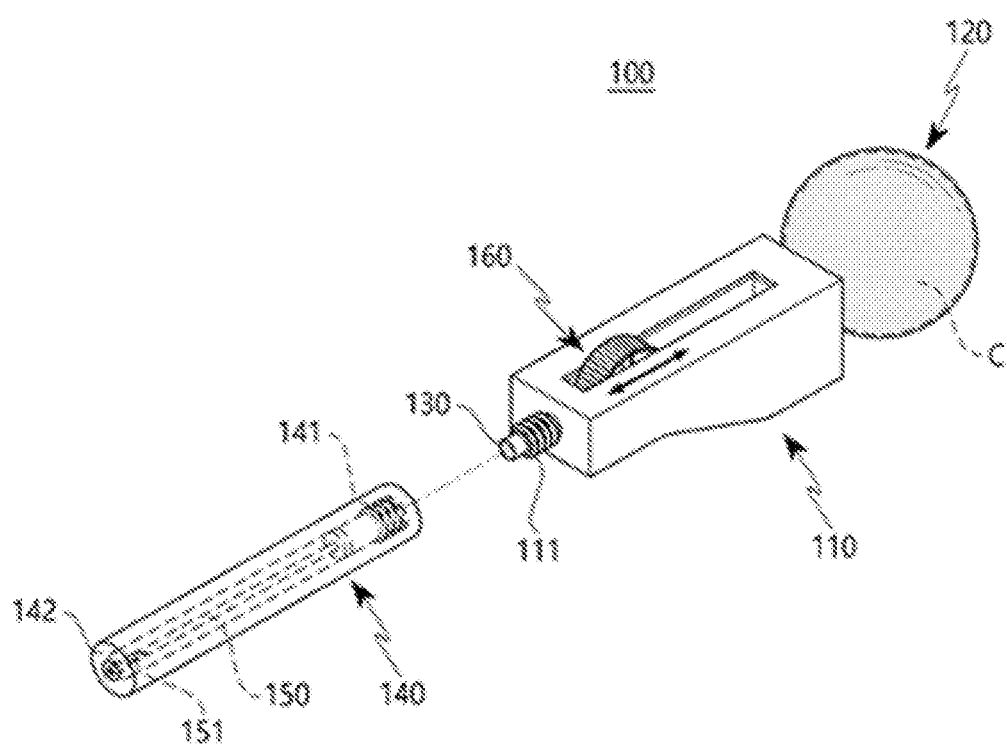
FIG. 2 is an exploded perspective view of the semiautomatic syringe.
Figure 3:
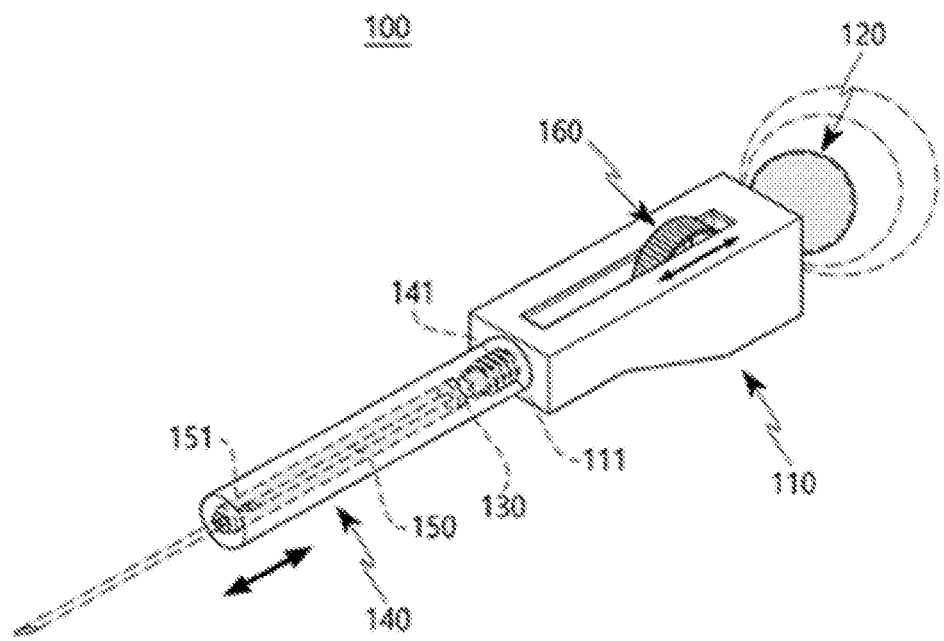
FIG. 3 is an exemplified view illustrating a state in which the semiautomatic syringe is used.
Figure 4A:
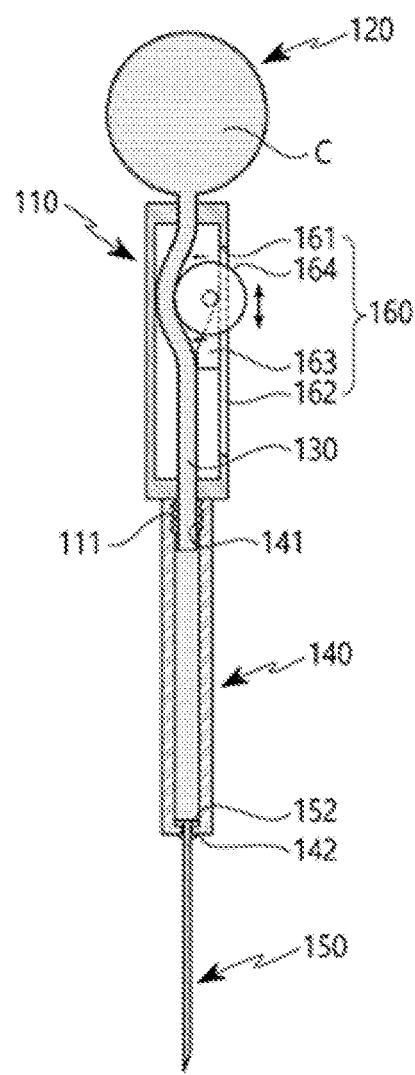
FIG. 4A and FIG. 4B are a cross-sectional side view illustrating a flow rate adjusting member of the semiautomatic syringe.
Figure 4B:
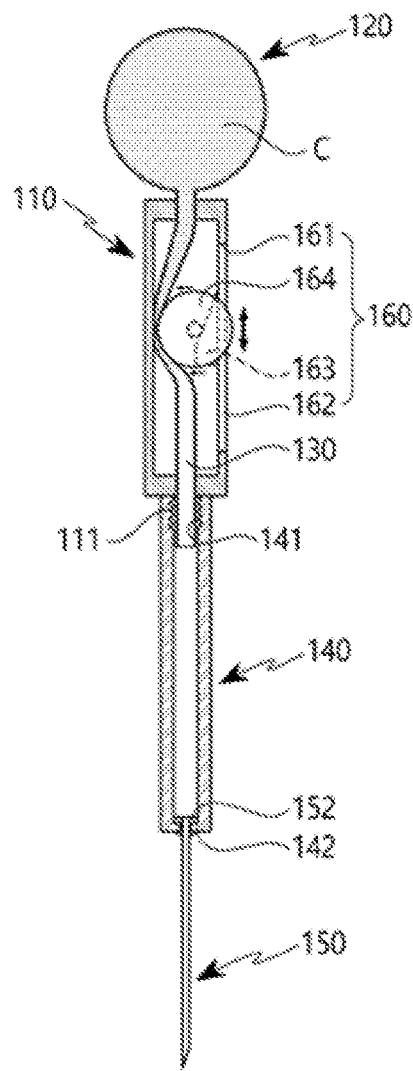
Figure 5A:
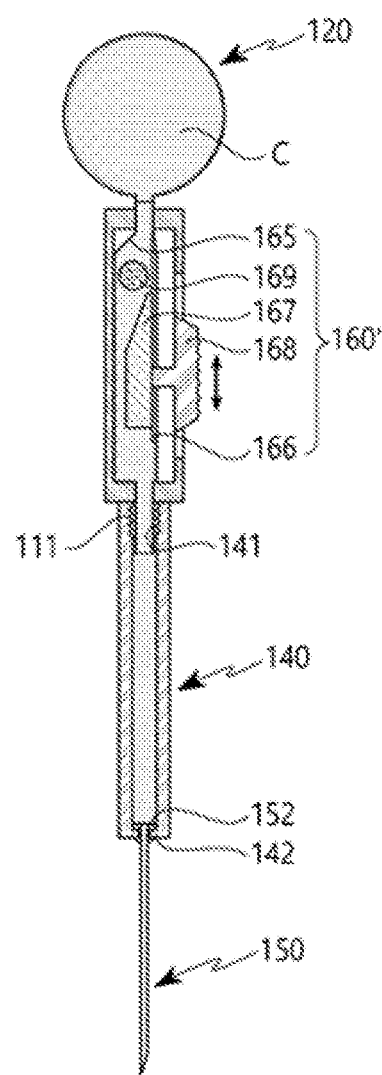
FIG. 5A and FIG. 5B are a cross-sectional side view illustrating a flow rate adjusting member according to another exemplary embodiment of the present invention.
Figure 5B:
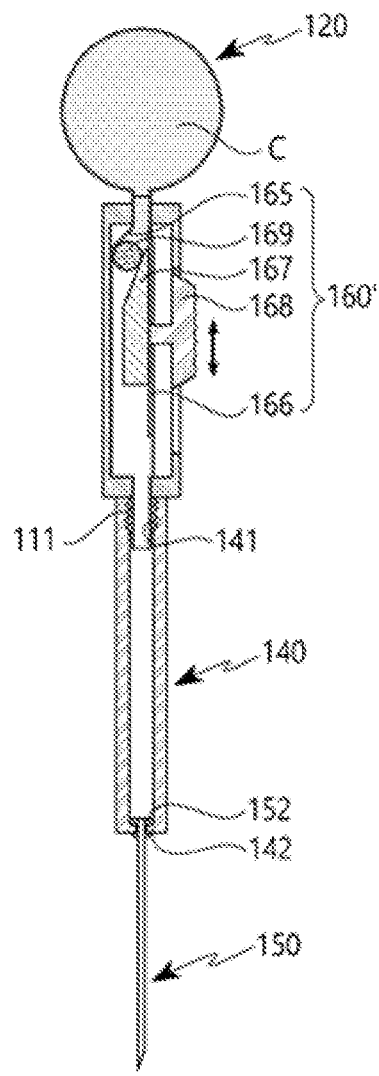

FIG. 1 is a perspective view of a semiautomatic syringe with improved safety according to an exemplary embodiment of the present invention, FIG. 2 is an exploded perspective view of the semiautomatic syringe, FIG. 3 is an exemplified view illustrating a state in which the semiautomatic syringe is used, FIG. 4A and FIG. 4B are a cross-sectional side view illustrating a flow rate adjusting member of the semiautomatic syringe, and FIG. 5A and FIG. 5B are a cross-sectional side view illustrating a flow rate adjusting member according to another exemplary embodiment of the present invention.

As illustrated in FIGS. 1 to 5B, a semiautomatic syringe 100 with improved safety according to the present invention may include a main body 110, a receptacle 120, an infusion solution tube 130, a protective cover 140, an injection needle 150, and a flow rate adjusting member 160 or 160'.

The main body 110 has a structure that may fix and support all components, to be described below, to maintain shapes of the components, and the main body 110 may be manufactured in the form of a housing having therein a hollow portion, but the main body 110 may be configured by, but not limited to, multiple frames.

The main body 110 may be made of a polyvinyl chloride (PVC) material that is easy to process, but the material of the main body 110 is not limited thereto, and various publicly known plastic materials may be applied within the technical scope of the present invention.

The receptacle 120 receives, accommodates and stores the set amount of various types of therapeutic infusion solutions C and supplies the infusion solution C to the infusion solution tube 130 to be described below, and the receptacle 120 may be installed at one side of the main body 110 and coupled to the infusion solution tube 130. According to the present invention, the receptacle 120 may be manufactured to receive therein the set amount of the infusion solution C and have a set pressure.

More specifically, during a process of manufacturing the receptacle 120, the receptacle 120 may be manufactured as a restoring member which has an internal pressure set, in a state in which the restoring member expands by receiving the infusion solution C, and contracts by its own restoring force when a passageway of the infusion solution tube 130 is opened, thereby discharging the received infusion solution C to the infusion solution tube 130 as the internal pressure is changed.

Here, the receptacle 120 is made of an elastic rubber material, and the internal pressure may be set in accordance with a thickness of the manufactured receptacle 120. The receptacle 120 may be variously designed and manufactured in consideration of an injection rate in accordance with the therapeutic purpose of the infusion solution C and the type of infusion solution C by those skilled in the art within the technical scope of the present invention.

The receptacle 120 has a thin rubber film shape when the receptacle 120 receives no infusion solution C, and has a rubber ball shape when the receptacle 120 receives the infusion solution C.

The infusion solution tube 130 provides a passageway for moving the infusion solution C. According to the present invention, the infusion solution tube 130 may extend by a set length while penetrating the main body 110 and may connect with the receptacle 120.

The infusion solution tube 130 may be manufactured in the form of a pipe having a hollow portion, and the material of the infusion solution tube 130 may be silicone, but because this configuration is a generally and publicly known technology, the infusion solution tube 130 may of course be variously modified and designed by those skilled in the art.

The protective cover 140 serves to cover the injection needle 150, to be described below, to improve safety, and the protective cover 140 may be installed at the other side of the main body 110 and may connect with the infusion solution tube 130. The protective cover 140 may extend by a set length and may have a hollow portion for accommodating the injection needle 150.

In addition, the protective cover 140 according to the present invention is separably coupled to the main body 110, and to this end, a first screw thread 111 and a second screw thread 141, which corresponds to the first screw thread 111, may be formed on coupling portions of the main body 110 and the protective cover 140, respectively.

Therefore, the protective cover 140 may be easily separated from and coupled to the main body 110, such that it is possible to replace not only the protective cover 140, but also the injection needle 150 provided in the hollow portion of the protective cover 140, thereby achieving a more hygienic usage.

The injection needle 150 serves as a needle for discharging and injecting the infusion solution C, which moves through the infusion solution tube 130, to the outside (into an injection target), and may be provided in the hollow portion of the protective cover 140, and an injection hole 151 having a set size may be penetratively formed in a longitudinal direction at a center of the injection needle 150 in order to discharge the infusion solution C that fills the protective cover 140 from the receptacle 120 through the infusion solution tube 130.

In addition, according to the present invention, the injection needle 150 may be provided to be inserted into the hollow portion of the protective cover 140, and a part of the injection needle 150 may automatically protrude to the outside of the protective cover 140 due to a change in pressure in the receptacle 120 when the passageway of the infusion solution tube 130 is opened by adjusting the flow rate adjusting member 160 or 160' to be described below.

With the aforementioned configuration, the injection needle 150 may instantaneously protrude in a pop-up manner as the pressure set in the receptacle 120 is high, and this configuration may be appropriately utilized when quick and instantaneous injection is required.

Here, the injection needle 150 may be formed to have a length relatively shorter than a length of the protective cover 140 so that the injection needle 150 is completely inserted into the protective cover 140.

In addition, a fixing portion 142, which extends in a centrifugal direction, may be provided at an end of the protective cover 140, which is opposite to the side where the second screw thread 141 is formed, to fix the injection needle 150 in a state in which a part of the injection needle 150 protrudes to the outside of the protective cover 140, and the injection needle 150 may be provided with a flange 152 that protrudes so that one end of the flange 152 is caught by the fixing portion 142.

The flow rate adjusting member 160 or 160' is configured to adjust a movement amount of the infusion solution C while opening and closing the passageway of the infusion solution tube 130, and the flow rate adjusting member 160 or 160' may be installed in the main body 110. According to the present invention, the flow rate adjusting member 160 or 160' may be the flow rate adjusting member 160 of a tube pressing structure type according to a first exemplary embodiment or the flow rate adjusting member 160' of a passageway closing structure type according to a second exemplary embodiment.

First, the flow rate adjusting member 160 of the tube pressing structure type according to the first exemplary embodiment may include a guide groove 161, a support portion 162, a catching projection 163, and a pressing roller 164

The guide groove 161 is a groove formed in a longitudinal direction of the main body 110 and serves to provide a movement route of the pressing roller 164 to be described below.

Here, in a case in which the main body 110 has a frame structure, the movement route of the pressing roller 164 may be provided autonomously by the main body 110, and thus the guide groove 161 may be omitted.

The support portion 162 is a structure formed in the guide groove 161 or the main body 110 in the longitudinal direction and serves to support the catching projection 163 to be described below.

The catching projection 163 serves to provide the movement route in an inward direction of the pressing roller 164, that is, a direction toward the position of the infusion solution tube 130, and the catching projection 163 may have an inclined surface inclined inward from the support portion 162 and may protrude to face the infusion solution tube 130.

The pressing roller 164 is a roller that directly presses the infusion solution tube 130, and the pressing roller 164 may be coupled to the guide groove 161 so that a central axis of the pressing roller 164 traverses the inclined surface of the catching projection 163. The pressing roller 164 adjusts a degree of pressing the infusion solution tube 130 by being closely attached to or spaced apart from the infusion solution tube 130 while being moved along the guide groove 161 and the inclined surface by external force.

That is, the flow rate adjusting member 160 of the tube pressing structure type, which is configured as described above, is structured to close or open the passageway while pressing the infusion solution tube 130 itself and changing an external shape of the infusion solution tube 130, thereby adjusting a flow rate of the infusion solution C.

Meanwhile, the flow rate adjusting member 160' of the passageway closing structure type according to the second exemplary embodiment may include an enlarged portion 165, a watertight guide groove 166, a pressing clamp 167, a guider 168, and a pressing ball 169.

The enlarged portion 165 serves to ensure an installation space of the pressing clamp 167 and the pressing ball 169 to be described below, and may protrude at a part of the infusion solution tube 130 so that the passageway is enlarged.

The watertight guide groove 166 is a groove that provides a movement route of the guider 168 to be described below, and the watertight guide groove 166 may be formed in a longitudinal direction at a side facing the enlarged portion 165. More particularly, the watertight guide groove 166 may be sealed with various publicly known elastic materials so as to be hydraulically sealed in order to prevent a leak of the infusion solution C to the outside of the infusion solution tube 130. This configuration related to the hydraulic sealing is not limited to the exemplary embodiment of the present invention, but may of course be variously modified and designed by those skilled in the art.

The pressing clamp 167 serves to close the passageway of the infusion solution tube 130, together with the pressing ball 169 to be described below, while coming into contact with the pressing ball 169, and the pressing clamp 167 may be installed in the enlarged portion 165 and may have an inclined surface at one side thereof.

The guider 168 is a handle which is exposed to the outside of the infusion solution tube 130 so that a user may hold the guider 168 and apply external force, and the guider 168 is connected to the pressing clamp 167 and may be exposed to the outside of the infusion solution tube 130 through the watertight guide groove 166. The guider 168 correspondingly moves the pressing clamp 167 while sliding along the watertight guide groove 166 by external force.

The pressing ball 169 is a ball that serves to close or open the passageway of the infusion solution tube 130, together with the pressing clamp 167, and the pressing ball 169 is installed in the enlarged portion 165 and serves to close or open the passageway of the infusion solution tube 130 while being closely attached to or spaced apart from the inclined surface of the pressing clamp 167 in accordance with the movement of the guider 168.

That is, the flow rate adjusting member 160' of the passageway closing structure type, which is configured as described above, is structured to directly close or open the hollow passageway in the infusion solution tube 130, thereby adjusting a flow rate of the infusion solution C.

Therefore, the semiautomatic syringe 100 with improved safety according to the present invention may be used more conveniently, economically, and safely with the configuration in which the infusion solution C may be automatically injected by the contraction of the receptacle 120 made of rubber, and the configuration in which the injection needle 150 is inserted into the protective cover 140, and the injection needle 150 protrudes in a pop-up manner by a change in pressure in the receptacle 120 only when the injection needle 150 is used.

In addition, the flow rate adjusting member 160 or 160' for opening and closing the movement passage of the infusion solution C is additionally installed, and the configuration of the flow rate adjusting member 160 and 160' is designed as the comparatively simple tube pressing structure 160 or passageway closing structure 160', and as a result, it is possible to freely and easily adjust a flow rate of the infusion solution C, simplify processes, and reduce production costs.

In addition, since the protective cover 140 is configured to be separable from the main body 110, it is possible to freely replace not only the protective cover 140 but also the injection needle 150, thereby enabling a hygienic usage.

While the present invention has been described above with reference to the exemplary embodiments, it will be apparent to those skilled in the art that the technical spirit of the present invention is not limited to the exemplary embodiments, but alterations and modifications can be made within the scope defined by the claims, and the alterations and the modifications also fall within the scope of the claims.

DESCRIPTION OF REFERENCE NUMERALS

C: infusion solution
100: semiautomatic syringe
110: main body
111: first screw thread
120: receptacle
130: infusion solution tube
140: protective cover
141: second screw thread
142: fixing portion
150: injection needle
151: injection hole
152: flange
160, 160': flow rate adjusting member
161: guide groove
162: support portion
163: catching projection
164: pressing roller
165: enlarged portion
166: watertight guide groove
167: pressing clamp
168: guider
169: pressing ball

INDUSTRIAL APPLICABILITY

According to the present invention, the semiautomatic syringe with improved safety may be used more conveniently, economically, and safely with the configuration in which the infusion solution may be automatically injected by the contraction of the receptacle made of rubber, and the configuration in which the injection needle is inserted into the protective cover, and the injection needle protrudes in a pop-up manner by a change in pressure in the receptacle only when the injection needle is used.

The invention claimed is:
1. A semiautomatic syringe with improved safety comprising:
 a main body;
 a receptacle which is installed at one side of the main body, is configured to receive therein a set amount of an infusion solution, and is configured to have a set pressure;
 an infusion solution tube which extends by a set length while penetrating the main body, connects with the receptacle, and provides a passageway for moving the infusion solution;
 a protective cover which is installed at the other side of the main body, connects with the infusion solution tube, extends by a set length, and has a hollow portion;
 an injection needle which is provided in the protective cover and has an injection hole formed to discharge the infusion solution, which moves through the infusion solution tube, to an outside; and a flow rate adjusting member installed in the main body, the flow rate adjusting member configured to adjust a movement amount of the infusion solution by opening and closing the passageway of the infusion solution tube, wherein the injection needle is provided in a state of being inserted into the hollow portion of the protective cover, and a part of the injection needle protrudes to the outside of the protective cover by a change in pressure in the receptacle when the passageway of the infusion solution tube is opened, and wherein the flow rate adjusting member includes,
- a guide groove formed in the main body, in a longitudinal direction,
- a support portion formed in the guide groove in the longitudinal direction,
- a catching projection having an inclined surface, which is inclined inward from the support portion, and protruding to face the infusion solution tube, and
- a pressing roller coupled to the guide groove so that a central axis of the pressing roller traverses the inclined surface of the catching projection, and is configured to adjust a degree of pressing the infusion solution tube by being closely attached to or spaced apart from the infusion solution tube while being moved along the guide groove and the inclined surface by external force.

2. The semiautomatic syringe with improved safety of claim 1, wherein the receptacle is a restoring member which has an internal pressure set in a state in which the restoring member expands by receiving the infusion solution, contracts by restoring force when the passageway of the infusion solution tube is opened, and discharges the received infusion solution to the infusion solution tube as the internal pressure is changed.

3. The semiautomatic syringe with improved safety of claim 1, wherein the protective cover is configured to be separably coupled to the main body.

4. A semiautomatic syringe with improved safety comprising:
- a main body;
- a receptacle which is installed at one side of the main body, is configured to receive therein a set amount of an infusion solution, and is configured to have a set pressure;
- an infusion solution tube which extends by a set length while penetrating the main body, connects with the receptacle, and provides a passageway for moving the infusion solution;
- a protective cover which is installed at the other side of the main body, connects with the infusion solution tube, extends by a set length, and has a hollow portion;
- an injection needle which is provided in the protective cover and has an injection hole formed to discharge the infusion solution, which moves through the infusion solution tube, to an outside; and
- a flow rate adjusting member installed in the main body, the flow rate adjusting member configured to adjust a movement amount of the infusion solution by opening and closing the passageway of the infusion solution tube, wherein the injection needle is provided in a state of being inserted into the hollow portion of the protective cover, and a part of the injection needle protrudes to the outside of the protective cover by a change in pressure in the receptacle when the passageway of the infusion solution tube is opened, and wherein the flow rate adjusting member includes,
- an enlarged portion which protrudes at a part of the infusion solution tube so that the passageway is enlarged,
- a watertight guide groove formed in a longitudinal direction at a side facing the enlarged portion and hydraulically sealed by elastic sealing processing,
- a pressing clamp installed in the enlarged portion and having an inclined surface at one side thereof,
- a guider which is connected to the pressing clamp and exposed to the outside of the infusion solution tube through the watertight guide groove so as to be held by a user, and is configured to correspondingly move the pressing clamp while sliding along the watertight guide groove by external force, and
- a pressing ball which is installed in the enlarged portion and closes or opens the passageway of the infusion solution tube by being closely attached to or spaced apart from the inclined surface of the pressing clamp in accordance with a movement of the guider.

* * * * *